(12) United States Patent
Borja

(10) Patent No.: US 9,408,780 B2
(45) Date of Patent: Aug. 9, 2016

(54) DENTURE ADHESIVE HYDROGEL WITH DRY TACK

(75) Inventor: Michael J. Borja, Keyport, NJ (US)

(73) Assignee: COMBE INCORPORATED, White Plains, NY (US)

(*) Notice: Subject to any disclaimer, the term of this patent is extended or adjusted under 35 U.S.C. 154(b) by 0 days.

(21) Appl. No.: 13/359,202

(22) Filed: Jan. 26, 2012

(65) Prior Publication Data

US 2013/0195771 A1 Aug. 1, 2013

(51) Int. Cl.

| | |
|---|---|
| *A61K 6/083* | (2006.01) |
| *A61K 47/32* | (2006.01) |
| *A61K 31/56* | (2006.01) |
| *A61K 6/097* | (2006.01) |
| *A61K 38/28* | (2006.01) |
| *A61P 35/00* | (2006.01) |
| *A61P 31/00* | (2006.01) |
| *A61P 29/00* | (2006.01) |
| *A61P 23/00* | (2006.01) |
| *A61P 31/10* | (2006.01) |
| *A61K 6/00* | (2006.01) |
| *C09J 171/02* | (2006.01) |
| *C09J 135/08* | (2006.01) |

(52) U.S. Cl.
CPC ............. *A61K 6/0026* (2013.01); *A61K 6/0061* (2013.01); *A61K 6/0067* (2013.01); *C09J 135/08* (2013.01); *C09J 171/02* (2013.01)

(58) Field of Classification Search
USPC ........................................................ 523/120
See application file for complete search history.

(56) References Cited

U.S. PATENT DOCUMENTS

| | | | |
|---|---|---|---|
| 3,736,274 A | 5/1973 | Schoenholz et al. | |
| 4,373,036 A | 2/1983 | Chang et al. | |
| 4,758,630 A | 7/1988 | Shah et al. | |
| 4,980,391 A | 12/1990 | Kumar et al. | |
| 5,001,170 A | 3/1991 | Keegan | |
| 5,037,924 A | 8/1991 | Tazi et al. | |
| 5,061,182 A | 10/1991 | Kubo et al. | |
| 5,073,604 A | 12/1991 | Holeva et al. | |
| 5,075,107 A | 12/1991 | Katakura et al. | |
| 5,093,387 A | 3/1992 | Schobel et al. | |
| 5,298,534 A | 3/1994 | Prosise et al. | |
| 5,436,283 A | 7/1995 | Okada et al. | |
| 5,513,988 A | 5/1996 | Jeffer et al. | |
| 5,525,652 A | 6/1996 | Clarke et al. | |
| 5,760,102 A | 6/1998 | Hall et al. | |
| 6,294,594 B1 | 9/2001 | Borja et al. | |
| 6,355,706 B1 | 3/2002 | Rajaiah et al. | |
| 6,475,498 B1 | 11/2002 | Rajaiah et al. | |
| 6,583,225 B1 | 6/2003 | Plochocka et al. | |
| 6,677,391 B1 | 1/2004 | Rajaiah et al. | |
| 6,706,817 B2 | 3/2004 | Plochocka et al. | |
| 7,008,976 B2 | 3/2006 | Rajaiah et al. | |
| 7,288,597 B2 | 10/2007 | Plochocka et al. | |
| 7,312,256 B2 | 12/2007 | Borja | |
| 7,834,066 B2 | 11/2010 | Rajaiah et al. | |
| 2004/0028930 A1* | 2/2004 | Wong et al. | 428/500 |
| 2007/0178055 A1* | 8/2007 | Buch et al. | 424/53 |
| 2008/0292669 A1 | 11/2008 | Deng et al. | |
| 2009/0239972 A1 | 9/2009 | Rajaiah et al. | |
| 2010/0298463 A1 | 11/2010 | Adusumilli et al. | |
| 2011/0094415 A1 | 4/2011 | Rajaiah et al. | |
| 2011/0223563 A1 | 9/2011 | Rajaiah et al. | |
| 2012/0244103 A1* | 9/2012 | Davis et al. | 424/78.02 |

FOREIGN PATENT DOCUMENTS

| | | | | |
|---|---|---|---|---|
| CA | 2369735 A1 | 10/2000 | | |
| GB | 1444485 A | 7/1976 | | |
| WO | WO 93/06144 | * | 4/1993 | |
| WO | WO93/06144 | * | 4/1993 | ............ C08F 267/04 |
| WO | 2011027216 A2 | 3/2011 | | |
| WO | 2011031519 A2 | 3/2011 | | |

OTHER PUBLICATIONS

European Search Report Application No. EP 13 15 2691 Completed:May 17, 2013; Mailing Date: May 28, 2013 8 pages.
Norcliff Thayer, et al.; "Polymer Mixtures as Adhesive for Denture"; May 28, 1988; 1 page abstract.
Canadian Intellectual Property Office Application No. 2,804,440 Mailing Date: May 21, 2015 pp. 3.

* cited by examiner

*Primary Examiner* — Walter Webb
(74) *Attorney, Agent, or Firm* — St Onge Steward Johnston and Reens LLC

(57) ABSTRACT

A dry tack denture adhesive hydrogel comprising a mixed salt of a copolymer of alkyl vinyl ether and maleic anhydride or maleic acid, a hygroscopic nonionic polymer, and water is provided. A method for preparation of the denture adhesive hydrogel is also disclosed.

22 Claims, No Drawings

DENTURE ADHESIVE HYDROGEL WITH DRY TACK

FIELD OF THE INVENTION

This invention relates to dental compositions based on blends of particular constituents and to the process of making such compositions, in particular to formulations and processes for making denture adhesives.

BACKGROUND OF THE INVENTION

Denture adhesives are used to assist a denture's ability to adhere to the gums. Denture adhesives are typically characterized as contributing an adhesive function once exposed to the moisture in a person's mouth and dissolve in the mouth over the course of a day.

A conventional approach is to provide an adhesive material made of a resin in the form of a powder or paste, which can be either natural or synthetic. Each time a user needs to apply a denture to the gum, the user takes the required amount of a denture base stabilizing material from a tube in the case of a powder or paste. Conventional denture adhesives in the form of pastes and powders are highly hydrophilic and readily absorb moisture forming an adhesive gel. One example is conventional Gantrez-based denture adhesives, which are applied to the denture and activated by saliva when the denture is first inserted into the mouth. These pastes and powders can be problematic for denture users. Once inserted, force is applied to the denture in order to spread the paste or power and ensure a snug fit of the denture to the gums. The force of application will cause the gums to displace the paste or gel that is formed and these adhesives will typically ooze or squirt out the side of the denture. This is known as primary ooze and is considered by many denture users as objectionable. Pastes and powders can be difficult to use because they require the denture wearer to ensure that the paste or powder is uniformly applied and in the right amount. Similar and other types of soft denture liners or adhesives have been disclosed in U.S. Pat. Nos. 5,061,182, 5,075,107, 5,436,283, and 5,513,988.

One approach for solving the problems of conventional denture adhesives is to provide a denture liner with mucoadhesive properties. U.S. Pat. No. 7,312,256 attempts to resolve known deficiencies in the art by providing a denture liner with a hydrophobic polymer component, such as polyethyl methacrylate, an esterified copolymer of methyl vinyl ether and maleic anhydride, polyvinyl acetate that inhibits the liner from absorbing moisture, a plasticizing component such as glycerol triacetate, an adhesive component such as sodium carboxymethylcellulose or polyethylene oxide.

Another approach, disclosed in U.S. Pat. Nos. 6,583,225, 6,706,817, and 7,288,597, is to form a hydrogel through the cross-linking reaction between an acidic polymer, particularly copolymers of maleic anhydride or maleic acid, and a comonomer, e.g. an alkylvinylether, with a suitable crosslinking agent, such as glycerol, in the presence of an esterification or amidization catalyst, such as sulfuric acid. The disclosed hydrogel is a covalently bound, ester and/or amide/imide crosslinked hydrogel that is extremely swellable in the presence of moisture. This hydrogel would be tacky in the unswelled state, but tackiness diminishes as swelling increases. Such a product would not function effectively as a denture adhesive because any significant swelling upon exposure to saliva would adversely affect adhesion and bite. As a result, an additional layer or component of a conventional denture adhesive would likely need to be included with the hydrogel to ensure proper adhesion of the denture to the gums.

U.S. Pat. No. 7,008,976 discloses a denture adhesive composition comprising mixed salts of an alkyl vinyl ether-maleic acid or maleic anhydride copolymer and/or terpolymer with isobutylene. While the denture adhesive is said to have improved adhesion, a non-adhesive self-supporting layer is used with the denture adhesive to maintain strength and provide integrity for the adhesive in the presence of water and/or saliva.

Thus, despite the above-noted technologies as well as many others, a need still exists for denture adhesive compositions providing improved hold. It is an object of the present invention to provide a hydrogel with improved adhesive properties to serve as a denture adhesive. It is another object that such a hydrogel have an immediate or quick onset of adhesive action and avoids the deficiencies associated with primary ooze. It is a further object of the present invention that such a hydrogel has a dry tack. It is still a further object of the present invention to provide a hydrogel denture adhesive that is resistant to dissolving over an extended period of time in the presence of water so as to provide an adhesive with an extended lifetime for effective use.

SUMMARY OF THE INVENTION

These and other objects are achieved by providing a Gantrez hydrogel comprising calcium, zinc, strontium, ferric, monovalent and bivalent cations, and a polyvinylpyrrolidone ("PVP") based tack agent. In a preferred embodiment, the monovalent cation is sodium and the bivalent cation is calcium, and thus the Grantrez hydrogel comprising sodium, calcium, zinc, strontium and ferric cations.

Prior to the present invention, PVP was only known as a processing aid for the manufacture of denture adhesives. The inventor has discovered that PVP, when combined with the cationic salts of the Grantrez hydrogel, creates an unexpected synergistic effect of promoting the dry tack of the hydrogel. As a result of the synergistic combination of PVP and the cationic salts, the hydrogel of the present invention not only provides improved adhesive and cohesive properties over extended time, but also has a dry tack property.

In one aspect, the present invention is directed to denture adhesive hydrogel compositions which comprise mixed salts of AVE/MA copolymer in an amount of about 25% to about 50% by weight of the hydrogel, wherein the mixed salts of the copolymer consisting essentially of a bivalent cation, and a monovalent cation; a humectant in an amount of about 5% to about 30% by weight of the hydrogel; a calcium compound in an amount of about 0.05% to about 10% by weight of the hydrogel; a zinc compound in an amount of about 0.05% to about 0.5% by weight of the hydrogel; a strontium compound in an amount of about 0.05% to about 0.5% by weight of the hydrogel; a ferric compound in an amount of about 0.05 to about 2% by weight of the hydrogel; a tack agent in an amount of about 0.1% to about 5.0% by weight of the hydrogel, wherein said tack agent comprises PVP; and water in amount of about 0.1% to about 5.0% by weight of the hydrogel.

In the above compositions, the monovalent cation serves as a neutralizing agent in neutralizing the free acid of AVE/MA copolymer and all of the other cations serve as crosslinking agents in crosslinking AVE/MA copolymer. The monovalent cation is preferably an alkali metal cation, and more preferably, sodium. The bivalent cation is preferably an alkaline earth metal cation, and more preferably, calcium.

In accordance with one embodiment, the preferred cationic salts are in the form of sodium and calcium salts of AVE/MA copolymer, calcium hydroxide, zinc chloride, strontium chloride hexahydrate, and ferric subsulfate.

The humectant can be selected from the group consisting of glycerin, polyhydric alcohols, ethylene glycol, propylene glycol, polyethylene glycol, sorbitol, and combinations thereof. One preferred humectant is glycerin.

The denture adhesive hydrogel of the present invention may further include an additional ingredient selected from the group consisting of an antimicrobial agent, an antibiotic, an anti-inflammatory agent, a dental desensitizing agent, an anesthetic agent, an anti-fungal, an aromatic, insulin, a steroid, an anti-neoplastic, a colorant, a preservative, a flavor component, a fragrance component, a sensation component, and combinations thereof. In the event that an antimicrobial agent is used, it may also include anti-foaming agent. Additionally, the tack agent may further comprise polyethylene oxide and a cellulose derivative.

In another aspect, the present invention is directed to processes for making the denture adhesive hydrogel. In accordance with one embodiment, the processes comprises the step of: (a) mixing a humectant in an amount of about 5% to about 30% by weight of the hydrogel, a tack agent in amount of about 0.1% to about 5.0% by weight of the hydrogel, wherein the tack agent is PVP, and water in an amount of about 30% to about 70% by weight of the hydrogel, optionally followed by cooling after mixing; (b) mixing a premixed combination of a zinc compound in an amount of about 0.05% to about 0.5% by weight of the hydrogel, a strontium compound in an amount of about 0.05% to about 0.5% by weight of the hydrogel, and a ferric compound in an amount of about 0.05 to about 2% by weight of the hydrogel, optionally with heating and stirring, with the mixture of step (a), and optionally followed by cooling; (c) mixing a calcium compound, preferably calcium hydroxide, in an amount of about 0.05% to about 10% by weight of the hydrogel, with the mixture of step (b); and (d) dispersing mixed salts of AVE/MA copolymer in an amount of about 25% to about 50% of the hydrogel to the mixture of step (c).

In the above processes, the mixture can be heated to an interior temperature from about 50° C. to about 80° C., and/or be cooled to an interior temperature from about 0° C. to about room temperature. In the event other ingredients are to be included in the hydrogel composition, they can be mixed in the first step with the humectant.

The present invention advantageously adds a calcium compound prior to dispersing a Grantrez hydrogel, regardless if calcium cations already exist in a Grantrez hydrogel. It is discovered that the additional calcium compound is useful to slow down the gelling process of the copolymer.

The processes can still further include the step of preparing the mixed salts of AVE/MA copolymer, which comprises the steps of: mixing an AVE/MA copolymer with a bivalent cation and a monovalent cation, heating the mixture in solution to a cross-linking temperature and forming the mixed salt of AVE/MA copolymer, and cooling the mixed salt of AVE/MA copolymer.

Other objects of the invention and its particular features and advantages will become more apparent from consideration of the accompanying description.

DETAILED DESCRIPTION OF THE INVENTION

The Denture Hydrogel Composition:

The denture adhesive hydrogel of the present invention comprises an AVE/MA copolymer, mono and multivalent cationic salts comprising sodium, calcium, zinc, strontium, ferric, a PVP based tack agent, a humectant, and water.

In accordance with some embodiments of the present invention, the denture adhesive hydrogel compositions comprise mixed salts of AVE/MA copolymer in an amount of about 25% to about 50% by weight of the hydrogel, wherein the mixed salts of the copolymer consists essentially of a bivalent cation and a monovalent cation; a humectant in an amount of about 5% to about 30% by weight of the hydrogel; a calcium compound in an amount of about 0.05% to about 10% by weight of the hydrogel; a zinc compound in an amount of about 0.05% to about 0.5% by weight of the hydrogel; a strontium compound in an amount of about 0.05% to about 0.5% by weight of the hydrogel; a ferric compound in an amount of about 0.05 to about 2% by weight of the hydrogel; a tack agent in an amount of about 0.1% to about 5.0% by weight of the hydrogel, wherein said tack agent comprises PVP; and water in amount of about 0.1% to about 5.0% by weight of the hydrogel.

The mixed salts of AVE/MA copolymer consist essentially of a bivalent cation and a monovalent cation. Both cations react with the acid group in the AVE/MA copolymer. The bivalent cation functions as both neutralizing and crosslinking agents, whereas the monovalent cation is just a neutralizing agent. The preferred bivalent cation is an alkaline earth metal cation, and more preferably is calcium. The preferred monovalent cation is an alkali metal cation, more preferably is sodium or potassium, and even more preferably is sodium.

The Ca/Na salts of poly (lower alkyl vinyl ether/maleic anhydride) are provided by the ISP Corporation of Wayne, N.J. under the tradename "Gantrez® MS-955." Gantrez® MS-955 is a mixed sodium and calcium salt of poly (methylvinyl ether/maleic acid) and is described by the chemical structural formula:

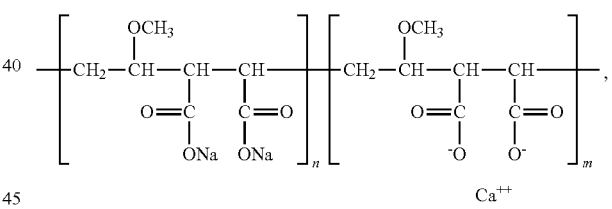

where n is an integer of 1 or greater, and m is an integer of 1 or greater. Gantrez® MS-955 used in the present invention may have a bivalent calcium hydroxide cation at a concentration of about 21.75% and the monovalent sodium hydroxide cation at a concentration of 1.95%.

Gantrez® MS-955 and other mixed salts of AVE/MA copolymer for use in the present invention can be made from reacting a copolymer of methyl vinyl ether and maleic anhydride described by the chemical structural formula:

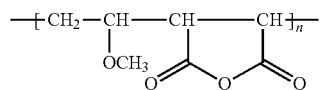

where n is an integer of 1 or greater, with a mixture of calcium and sodium salts.

A copolymer of methyl vinyl ether maleic anhydride is a water-insoluble white powder that can be easily dispersed in water where the polymeric anhydride hydrolyzes to produce a transparent solution of the free acid, i.e., a copolymer of methyl vinyl ether maleic acid.

The mixed salts of AVE/MA copolymer are hydrophilic which provides the adhesive characteristics of the hydrogel denture adhesive. The mixed salts of AVE/MA copolymer/ can be in an amount of about 25% to about 50% by weight of the hydrogel, preferably in an amount of about 25% to about 40% by weight of the hydrogel, and more preferably in an amount of about 30% by weight of the hydrogel.

Besides the calcium cation contained in the mixed salts of AVE/MA copolymer, the hydrogel composition may include additional calcium compound in an amount of about 0.05% to about 10% by weight of the hydrogel, preferably in an amount of about 0.5% by weight of the hydrogel. The additional calcium compound can be selected from the group consisting of calcium hydroxide, calcium acetate, calcium carbonate, calcium halides, calcium lactate, calcium oxide, calcium nitrate, calcium phosphate, calcium gluconate, and combinations thereof. One preferred calcium compound is calcium hydroxide.

It is discovered that the additional calcium compound is needed to slow down the gelling process of the copolymer. This discovery is unexpected because a calcium compound is known to crosslink the acids of the copolymer, which would normally lead to a faster gelling. Without wishing to be bound by the theory, it is believed that the additional calcium compound, introduced prior to the dispersing of the copolymer, interferes with the copolymer's access to water and thus slows down the gelling process. Because calcium cations may have already existed in Grantrez based hydrogel, a person of ordinary skill in the art, prior to the present invention, would not be likely to introduce the additional calcium compound in the composition.

Other salts in the compositions include the salts of zinc, ferric and strontium. Suitable salts of zinc, ferric and strontium should be water soluble and used in a safe and effective amount. The term "safe and effective adhesive amount," used hereinafter, means an amount sufficient to provide adherence to the gum, without toxicity to the user, damage to oral tissue, and alteration of the denture material.

Except for the monovalent cation, all of the other cations are either bivalent or trivalent cations which can function as crosslinking agents. The inclusion of the crosslinking agents can reduce the amount of AVE/MA polymer required in the hydrogel while maintaining the necessary properties of the hydrogel. While these cations can make the hydrogel cohesively strong, they may accelerate the gelling of the hydrogel during processing. Therefore, a balanced amount for each cation is preferably used in respect to the other ingredients in the formula to prevent uncontrollable gelling and to strike a balance between cohesion and adhesion.

The term "cohesion," used hereinafter, refers to the ability of hydrogel molecules stick directly to each other. A strong cohesive hydrogel typically has a longer dissolution time to allow for a longer hold time of the hydrogel when placed in the month.

The term "adhesion," used hereinafter, refers to the ability of a hydrogel to bond to the surface of the denture and to the gums. A hydrogel with good adhesion can provide an immediate onset of adhesive action and a long term hold to a surface.

The zinc compound can be zinc chloride, zinc oxide, or a combination thereof. The zinc compound can be in an amount of about 0.05% to about 0.5% by weight, and preferably about 0.1% by weight of the hydrogel.

The strontium compound can be selected from the group consisting of strontium chloride hexahydrate, strontium chloride and strontium citrate. A preferred strontium compound is strontium chloride hexahydrate. The strontium compound can be in an amount of about 0.05% to about 0.5% by weight, and preferably about 0.1% by weight of the hydrogel.

The ferric compound can be selected from the group consisting of ferric chloride hexahydrate, ferric chloride, ferric subsulfate, and combinations thereof. A preferred ferric compound is ferric subsulfate. The ferric compound can be in an amount of about 0.05 to about 2% by weight, and preferably about 0.22% by weight of the hydrogel.

The addition of the ferric compound is important to make the hold of the hydrogel last longer. In a consumer Home Use Test, a comparative denture adhesive hydrogel without the ferric compound failed in the test because the hold of the comparative hydrogel, while initially good, did not last. The differences between the hydrogel formulas with and without the ferric compound are more obvious in a "hydration test." The hydration test measures the dissolution rates of different hydrogels in water at 37° C. in a beaker. The hydration test shows that the dissolution time for the comparative hydrogel is one hour, and in contrast, the dissolution time for the hydrogel of the present invention is five hours. The magnitude differences in the dissolution times may be explained by the fact that a ferric cation, being a trivalent cation, is able to crosslink at three positions simultaneously, and thus makes the gel more tightly bound and leads to the dramatic difference in the dissolution time.

PVP is a nonionic water-soluble polymer. Due to its good water solubility and high hygroscopicity, PVP can be used as a processing aid for the manufacture of a denture adhesive. In the present invention, PVP was initially added to the formula of Gantrez hydrogel with the cationic salts to increase the viscosity of the formula in order to solve the hourglassing problem during the manufacture. Without PVP as a component in a hydrogel formula, the hydrogel has no sufficient yield stress when passed under a doctor blade which results in the hydrogel contracting into the shape of an hour glass. The addition of PVP to the hydrogel formula not only solves the hourglassing problem in the process to produce an evenly distributed wide and thin gel with very clean edges, but surprisingly, improves the dry tack of the hydrogel.

The term "dry tack," used hereinafter, means that a denture adhesive with a good dry tack property provides immediate bonding to surfaces.

The dry tack of an AVE/MA copolymer is often associated with the number of free acids in the AVE/MA copolymer. It is known that the unreacted or uncrosslinked free acid promotes dry tack. Because lesser free acid sites in the AVE/MA copolymer are available due to the increased crosslinking with the cationic salts, a hydrogel formulated with the cationic salts of AVE/MA copolymer tends to lose its dry tack, as indicated by a subjective test of dry tack. It is discovered, however, that the lost dry tack of the hydrogel can be recovered by adding only a little amount of PVP to the hydrogel formula. This result is unpredicted because PVP can form hydrogen bonds with the free acid groups in the mixed salts of AVE/MA copolymer which would make lesser free acid sites available. Thus, the addition of PVP theoretically would lead to less tack, rather than improved tack of the hydrogel. Without wishing to be bound by the theory, the addition of a small amount of PVC to the hydrogel not only improves yield stress but is believed to also add dry tack by partially plasticizing the hydrogel.

The PVP used in the present invention is provided by BASF under the tradename Kollidon 90F. The PVP can be used in an amount of about 0.1% to about 5.0%, preferably about 1%, by weight of the hydrogel.

The tack agent may further be polyethylene oxide or a cellulose derivative. Both agents not only add yield stress to the hydrogel, but it is believed that they also act as plasticizers which promotes dry tack. The cellulose derivative can be selected from the group consisting of sodium methylcellulose, sodium carboxymethylcellulose, hydroxyethylcellulose, sodium hydroxypropylcellulose, sodium hydroxypropylmethylcellulose, and mixtures thereof. A preferred cellulose derivative is sodium carboxymethylcellulose.

The humectant is used to provide a moistening effect to the hydrogel. The humectant also provides stability by limiting or controlling the rate at which the hydrogel denture adhesive absorbs water over time when placed in the mouth and thus controls the rate at which the mixed salts of AVE/MA copolymer hydrate and dissolve in the mouth.

The humectant can be in an amount of about 5% to about 30% by weight of the composition, preferably in an amount of about 10% to about 25% by weight of the hydrogel, most preferably in an amount of about 20% by weight of the hydrogel. Suitable humectants include, but are not limited to, glycerin, polyhydric alcohols such as ethylene glycol, propylene glycol, polyethylene glycol, and sorbitol, and combinations thereof. One preferred humectant is glycerin as it can provide therapeutic benefits of a warming sensation and lubricity in making the mouth feel better due to its emollient properties.

The denture adhesive according to the present invention can contain additional ingredients in a safe and effective amount. These ingredients can improve the functionality of the adhesive and/or provide ancillary benefits to the denture wearer.

The additional ingredients, which can be used in the denture adhesive in accordance with the present invention, include therapeutically active agents suitable for treating individuals in need thereof. These agents include antimicrobial agents, such as benzalkonium halides, quaternary ammonium salts, pyridinum salts, phosphonium salts, iodine, sulfonamides, bisbiguanides, or phenolics, antibiotics such as tetracycline, neomycin, kanamycin, metronidazole, or clindamycin, anti-inflammatory agents, such as aspirin, acetaminophen, naproxen and its salts, ibuprofen, ketorolac, flurbiprofen, indomethacin, eugenol, or hydrocortisone, dental desensitizing agents, such as potassium nitrate, strontium chloride or sodium fluoride, anesthetic agents, such as lidocaine or benzocaine; anti-fungals, aromatics, such as camphor, eucalyptus oil, and aldehyde derivatives, such as benzaldehyde; insulin, steroids, and anti-neoplastics. Certain forms of therapy and combinations of these agents in the same delivery system may be useful in order to obtain an optimal effect. It is preferable to provide cetylpyridinium chloride as an antimicrobial agent in an amount of about 0.01% to about 0.1% by weight of the hydrogel, preferably in an amount of about 0.03% to about 0.07% by weight of the hydrogel. In the event that an antimicrobial agent such as cetylpyridinium chloride is included in the hydrogel, it is preferable to further include an anti-foaming agent, such as simethicone, in an amount of about 0.005% to about 0.05% by weight of the hydrogel, preferably in an amount of about 0.01% to about 0.03% by weight of the hydrogel. It has been discovered that when forming a hydrogel in accordance with the present invention, the inclusion of cetylpyridinium chloride can cause gas bubbles to form within the hydrogel. An anti-foaming agent, such as simethicone, can be included in the preferred amounts to eliminate the presence of unwanted gas bubbles without adversely affecting the adhesive properties of the hydrogel. Other suitable additional ingredients include colorants and preservatives, such as methyl and propyl parabens. The denture adhesive compositions of the present invention may also include one or more components, which provide flavor, fragrance, and/or sensation benefit. These components include natural or artificial sweetening agents, menthol, menthyl lactate, wintergreen oil, peppermint oil, spearmint oil, leaf alcohol, as well as coolants 3-1-menthoxypropane-1,2-diol and paramenthane carboxamide agents, such as N-ethyl-p-menthane-3-carboxamide.

The particular combinations of the ingredients of the present invention provide a hydrogel with superior characteristics comparing to the prior art. First, the hydrogel of the present invention avoids the primary ooze problem associated with the use of the adhesive pastes and powders. This is because the hydrogel is preformed as a very thin material with a fixed surface area that does not change when the denture is inserted in the mouth, and thus no excess adhesive can ooze out from under the denture when the denture is inserted in the mouth. Second, the hydrogel also avoids the messy denture cleaning problems associated with the use of the paste or powder adhesives. Third, the hydrogel advantageously provides a natural feel to the denture users compared to the adhesive pastes and powders. This effect is caused by the high water content in the hydrogel and possibly the softening of the Gantrez molecules in the presence of salvia. Without wishing to be bound by theory, it is believed that tightly bound molecules of the Gantrez become less tightly bound in the presence of water (salvia), which makes the adhesive softer. Lastly, the hydrogel of the present invention is not only provides an immediate effective adhesion action, but also maintains the improved hold over an extended time when placed in the mouth.

The following are non-limiting examples of denture adhesives in accordance with the present invention.

EXAMPLE 1

| Component | Amount by weight % |
| --- | --- |
| DI Water | 30-70 |
| D&C Red No. 27 | >0.01 |
| Glycerin USP 99+% | 5-30 |
| Gantrez MS955 | 25-50 |
| Methyl Paraben | 0.05 |
| Calcium Hydroxide - additional | 0.05-10 |
| Zinc Chloride | 0.05-2 |
| Strontium Chloride Hexahydrate | 0.05-2 |
| Ferric Subsulfate | 0.05-2 |
| PVP | 0.1-5.00 |
| TOTAL | 100 |

EXAMPLES 2, 3 and 4

| Component | Amount by weight % (Example 2) | Amount by weight % (Example 3) | Amount by weight % (Example 4) |
| --- | --- | --- | --- |
| DI Water | 53.324 | 53.174 | 42.05 |
| D&C Red No. 27 | 0.01 | 0.1 | 0.01 |
| Glycerin USP 99+% | 15 | 15 | 10 |
| Gantrez MS955 | 30 | 30 | 45 |
| Methyl Paraben | 0.05 | 0.05 | 0.05 |
| Calcium Hydroxide - additional | 0.42 | 0.42 | 0.96 |
| Zinc Chloride | 0.019 | 0.019 | 0.07 |
| Strontium Chloride Hexahydrate | 0.037 | 0.037 | 0.14 |

-continued

| Component | Amount by weight % (Example 2) | Amount by weight % (Example 3) | Amount by weight % (Example 4) |
|---|---|---|---|
| Ferric Subsulfate | 0.14 | 0.29 | 0.72 |
| PVP | 1.0 | 1.0 | 1.0 |
| TOTAL | 100 | 100 | 100 |

The Processes for Preparation of the Denture Adhesive Hydrogel:

The processes for making the denture adhesive hydrogel comprise the steps of mixing all of the ingredients in the above compositions in a suitable vessel or container until a homogenous suspension or solution is formed.

In some embodiments, the processes for preparation of the adhesive hydrogel comprise the steps of: (a) mixing a humectant in an amount of about 5% to about 30% by weight of the hydrogel, a tack agent in an amount of about 0.1% to about 5.0% by weight of the hydrogel and water in an amount of about 30% to about 70% by weight of the hydrogel, wherein said tack agent comprises PVP in an amount of 0.1% to 5.0% by weight of the hydrogel; (b) mixing a premixed combination of a zinc compound in an amount of about 0.05% to about 0.5% by weight of the hydrogel, a strontium compound in an amount of about 0.05% to about 0.5% by weight of the hydrogel, and a ferric compound in an amount of about 0.05 to about 2% by weight of the hydrogel with the mixture of step (a); (c) mixing a calcium compound in an amount of about 0.05% to about 10% by weight of the hydrogel with the mixture of step (b); and (d) dispersing mixed salts of AVE/MA copolymer in an amount of about 25% to about 50% of the hydrogel to the mixture of step (c), wherein the mixed salt of said copolymer consisting essentially of a bivalent cation and a monovalent cation. Preferably, the mixing with the calcium compound in step (c) lasts for at least five seconds.

While the embodiments of the present invention disclose the particular order of adding each ingredient, the present invention is not limited to that order. In general, it is preferred to disperse the mixed salts of AVE/MA copolymer during the last step into the mixture of the rest of the ingredients. Optionally, the mixture from step (c) is cooled before the dispersing step. Additionally, the calcium compound is preferably added prior to the addition of the mixed salts of AVE/MA copolymer to control the gelling rate of the hydrogel based on the discovery that the calcium compound slows down the gelling rate of the hydrogel process. This discovery is unanticipated because calcium compounds are known to crosslink the acids of the copolymer and make less free acids available, which would normally lead to a faster gelling. Without wishing to be bound by the theory, it is believed that the calcium compound, introduced prior to the dispersing of the copolymer, interferes with the copolymer's access to water and thus slows down the gelling process. Further, since calcium cations have already existed in Grantrez based hydrogel, the introduction of an additional calcium compound in the process would not have been obvious to a person of ordinary skilled in the art prior to the present invention.

The introduction of PVP at the first step of the process is beneficial. PVP modifies the viscosity of the mixture to allow for an effective and smooth process and a uniform hydrogel. In a coating test which is used to evaluate the quality of hydrogels, the hydrogel manufactured in accordance with the present process is evenly distributed in width and thickness and has very clean edges. Overall, the processes of the present invention advantageously allow for the efficient production of a uniform hydrogel that is strong, tacky and with enhanced adhesive properties.

The term "mixture", used hereinafter, refers to a solution, slurry, or suspension. The term "mixing", used hereinafter, refers to stirring or other agitating means, including heating to facilitate the mixing and subsequently cooling of the mixture. Generally, the mixture can be heated to an interior temperature from about 50° C. to about 80° C. prior to or during the mixing. The interior temperature of the mixture may rise during the mixing even without exterior heating. In that event, vigorously stirring is necessary to evenly dissipate the heating for uniform mixing results. After each mixing step, the mixture may optionally be cooled to an interior temperature anywhere from about 0° C. to about room temperature, depending on the scale and exothermic nature of the next step. Cooling is preferred when the next step is exothermic.

In accordance with the present invention, a preferred humectant is glycerin, in an amount of about 20% by weight of the hydrogel; a preferred calcium compound is calcium hydroxide, in an amount of about 0.5% by weight of the hydrogel; a preferred zinc compound is zinc chloride, in an amount of about 0.1% by weight of the hydrogel; a preferred strontium compound is strontium chloride hexahydrate, in an amount of about 0.1% by weight of the hydrogel; and a preferred ferric compound is ferric subsulfate, in an amount of about 0.22% by weight of the hydrogel.

The tack agent may further comprise polyethylene oxide and a cellulose derivative. A preferred cellulose derivative in accordance with the present invention is sodium carboxymethylcellulose. In the process, the polyethylene oxide and the cellulose derivative are premixed with PVP to form the tack agent, before they are mixed with a humectant.

The hydrogel of the present invention may optionally include other ingredients which improve the functionality of the adhesive and/or provide ancillary benefits to the denture wearer. These ingredients can be mixed in the first step with the humectant, the tack agent and water.

The processes for making the adhesive hydrogel may also comprise a step of preparing the mixed salts of AVE/MA copolymer for use in the dispersion. The mixed salts of AVE/MA copolymer can be prepared from a copolymer of methyl vinyl ether and maleic anhydride described by the chemical structural formula:

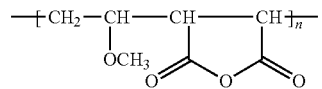

where n is an integer of 1 or greater.

Such copolymers are commercially available under the trade name Gantrez AN and include AN-119, AN-903, AN-139, and AN-169. The AVE/MA Salts can be made by mixing the AVE/MA Copolymer with a multivalent cation that serves as a cross linking agent and a monovalent cation that serves as a neutralizing agent. The multivalent cations are preferably alkali metal cations, most preferably magnesium and calcium. The monovalent cations are also preferably alkali metal cations, most preferably sodium and potassium cations. The mixture of the AVE/MA copolymer, multivalent cations and monovalent cations are placed in solution and the solution is heated to a copolymer cross-linking temperature, which can range from 85° C. to 110° C., forming the mixed salts of AVE/MA copolymer. After formation of the mixed salts of AVE/MA copolymer, the composition is cooled and any remaining water is removed. One example for forming the mixed salts of AVE/MA copolymer is in accordance with the following method: 1) dry mix 76.3 w/w % Gantrez AN-169 BF with 21.7 w/w % Ca(OH)2 and 2.0 w/w % NaOH; 2) combine the dry mixture with water in a reactor vessel to achieve a 5-15% solution/slurry; 3) heat the solution/slurry to 85° C. and mix for an hour; 4) transfer the solution/slurry to a drying tray and, flash off water via evaporation using an oven at 65° C.; and 5) cool and mill the material into a fine powder. Other examples for forming the AVE/MA Salt are disclosed in U.S. Pat. Nos. 4,373,036, 4,758,630, 4,980,391, 5,037,924, 5,073,604, 5,093,387, 5,298,534, and 5,525,652, which are incorporated herein by reference as if fully set forth herein.

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A denture adhesive hydrogel comprising:
   (a) a mixed salt of a copolymer of alkyl vinyl ether, and (i) maleic anhydride or (ii) maleic acid,
      wherein the mixed salt comprises monovalent and multivalent cationic salts selected from the group consisting of sodium, calcium, zinc, strontium, ferric and mixtures thereof;
   (b) a dry tack enhancing agent being polyvinylpyrrolidone, and optionally one or both of polyethylene oxide and a cellulose derivative, wherein the dry tack agent is in an amount of about 0.1% to less than 5.0% by weight of the hydrogel; and
   (c) water,
   wherein the hydrogel has a dry tack physical characteristic.

2. The denture adhesive hydrogel of claim 1, wherein said dry tack enhancing agent is polyvinylpyrrolidone.

3. The denture adhesive hydrogel of claim 1, wherein said cellulose derivative is selected from the group consisting of sodium methylcellulose, sodium carboxymethylcellulose, sodium hydroxyethylcellulose, sodium hydroxypropylcellulose, sodium hydroxypropylmethylcellulose, and mixtures thereof.

4. The denture adhesive hydrogel of claim 1, further comprising a compound selected from the group consisting of a calcium compound, a zinc compound, a strontium compound, a ferric compound, and mixtures thereof.

5. The denture adhesive hydrogel of claim 4, wherein:
   said calcium compound is selected from the group consisting of calcium hydroxide, calcium acetate, calcium carbonate, calcium halides, calcium lactate, calcium oxide, calcium nitrate, calcium phosphate, calcium gluconate, and combinations thereof;
   said zinc compound is selected from the group consisting of zinc chloride, zinc oxide, and combinations thereof;
   said strontium compound is selected from the group consisting of strontium chloride hexahydrate, strontium chloride, strontium citrate, and combinations thereof; and
   said ferric compound is selected from the group consisting of ferric chloride hexahydrate, ferric chloride, ferric subsulfate, and combinations thereof.

6. The denture adhesive hydrogel of claim 1, wherein said mixed salt of said copolymer includes a monovalent cation and a bivalent cation and is about 25% to about 50% by weight of the hydrogel.

7. The denture adhesive hydrogel of claim 1, wherein said water is about 35% to about 65% by weight of the hydrogel.

8. The denture adhesive hydrogel of claim 1, wherein said mixed salt includes an alkaline earth metal bivalent cation and an alkali metal monovalent cation.

9. The denture adhesive hydrogel of claim 5, wherein:
   said calcium compound is calcium hydroxide;
   said zinc compound is zinc chloride;
   said strontium compound is strontium chloride hexahydrate; or
   said ferric compound is ferric subsulfate.

10. The denture adhesive hydrogel of claim 5, wherein:
    said calcium compound is about 0.05% to about 10% by weight of the hydrogel;
    said zinc compound is about 0.05% to about 0.5% by weight of the hydrogel;
    said strontium compound is about 0.05% to about 0.5% by weight of the hydrogel; or
    said ferric compound is about 0.05% to about 2% by weight of the hydrogel.

11. The denture adhesive hydrogel of claim 1, further comprising a humectant.

12. The denture adhesive hydrogel of claim 11, wherein said humectant is selected from the group consisting of glycerin, polyhydric alcohols, ethylene glycol, propylene glycol, polyethylene glycol, sorbitol, and combinations thereof.

13. The denture adhesive hydrogel of claim 12, wherein said humectant is glycerin.

14. The denture adhesive hydrogel of claim 11, wherein said humectant is about 5% to about 30% by weight of the hydrogel.

15. The denture adhesive hydrogel of claim 1, further comprising an additional ingredient selected from the group consisting of an antimicrobial agent, an antibiotic, an anti-inflammatory agent, a dental desensitizing agent, an anesthetic agent, an anti-fungal, an aromatic, insulin, a steroid, an anti-neoplastic, a rheological agent, a colorant, a preservative, a flavor component, a fragrance component, a sensation component, and combinations thereof.

16. The denture adhesive hydrogel of claim 1, wherein the mixed salt comprises a trivalent ferric salt.

17. The denture adhesive hydrogel of claim 2, wherein said polyvinylpyrrolidone is in an amount of 1% by weight of the hydrogel.

18. The denture adhesive hydrogel of claim 17, wherein the mixed salt comprises a trivalent ferric salt.

19. The denture adhesive hydrogel of claim 16, wherein the mixed salt further comprises a sodium compound, a calcium compound, a zinc compound, and a strontium compound.

20. The denture adhesive hydrogel of claim 2,
    wherein the mixed salt of the copolymer of alkyl vinyl ether, and (i) maleic anhydride or (ii) maleic acid is about 30% by weight of the hydrogel;
    wherein polyvinylpyrrolidone is in an amount of from in an amount of about 0.1% to less than 5.0% by weight of the hydrogel;
    wherein the denture adhesive hydrogel further comprises sodium hydroxide in an amount of about 0.2% by weight of the hydrogel,
    calcium hydroxide in an amount of about 0.42% by weight of the hydrogel,
    zinc chloride in an amount of about 0.019% by weight of the hydrogel,
    strontium chloride hexahydrate in an amount of about 0.037% by weight of the hydrogel, and
    ferric subsulfate in an amount of about 0.21% by weight of the hydrogel.

21. The denture adhesive hydrogel of claim 20, wherein the denture adhesive hydrogel further comprises
   glycerin in an amount of about 15% by weight of the hydrogel,
   methyl paraben in an amount of about 0.05% by weight of the hydrogel, and
   red 27 lake in an amount of 0.01% by weight of the hydrogel.

22. The denture adhesive hydrogel of claim 21,
   wherein polyvinylpyrrolidone is in an amount of 1% or 4% by weight of the hydrogel;
   wherein water makes the weight balance of the hydrogel.

* * * * *